US008628492B2

(12) United States Patent
Lin et al.

(10) Patent No.: US 8,628,492 B2
(45) Date of Patent: Jan. 14, 2014

(54) IMPLANTABLE GLAUCOMA DRAINAGE DEVICE

(75) Inventors: Jeffrey Chun-Hui Lin, Pasadena, CA (US); Po-jui Chen, Mountain View, CA (US); Yu-Chong Tai, Pasadena, CA (US); Damien Craig Rodger, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 316 days.

(21) Appl. No.: 12/459,587

(22) Filed: Jul. 1, 2009

(65) Prior Publication Data

US 2010/0004635 A1    Jan. 7, 2010

Related U.S. Application Data

(60) Provisional application No. 61/133,699, filed on Jul. 1, 2008.

(51) Int. Cl.
*A61M 5/00* (2006.01)
(52) U.S. Cl.
USPC .................................... 604/9; 604/8
(58) Field of Classification Search
USPC ............... 604/8–10, 521; 606/107, 166, 153
See application file for complete search history.

(56) References Cited

U.S. PATENT DOCUMENTS

| 5,092,837 | A  | * | 3/1992 | Ritch et al. ..................... 604/8 |
| 6,780,164 | B2 | * | 8/2004 | Bergheim et al. ............... 604/8 |
| 7,394,182 | B2 | * | 7/2008 | Pelrine et al. ................. 310/328 |
| 2008/0228127 | A1 | * | 9/2008 | Burns et al. ..................... 604/9 |
| 2010/0010416 | A1 | * | 1/2010 | Juan et al. ....................... 604/9 |

OTHER PUBLICATIONS

P.J. Chen, et al., "Surface-Micromachined Parylene Dual Valves for On-Chip Unpowered Microflow Regulation," J. Micoelectromech. Syst., vol. 16, pp. 223-231, 2007.*
P.J. Chen, et al., "Floating-Disk Parylene Micro Check Valve," Proc. MEMS 2007 Conference, Kobe, Japan, Jan. 21-55, 2007, pp. 453-456.
P.J., et al., "Floating-Disk Parylene Microvalve for Self-Regulating Biomedical Flow Controls," Proc. MEMS 2008 Conference, Tucson, AZ, USA, Jan. 13-17, 2008, pp. 575-578.
P.J. Chen, et al., "Implementation of microfabricated suture-less flexible parylene tissue anchors on minimally invasive biomedical implants," Proc. MicroTAS 2007 Conference, Paris, France, Oct. 7-11, 2007, pp. 518-520.

* cited by examiner

*Primary Examiner* — Philip R Wiest
(74) *Attorney, Agent, or Firm* — Tope-McKay & Associates (57) ABSTRACT

An implantable glaucoma drainage device (GDD) system is disclosed. The GDD system comprises a microflow control system for controlling intraocular pressure, a protective capillary carrier tube housing the microflow control system, and anchoring arms holding the implanted device in place. The overall GDD size can be in a needle-implantable form factor for minimally invasive implantation. The GDD may be implanted via subconjunctival needle implantation to mimic the normal aqueous humor drainage pathway.

4 Claims, 9 Drawing Sheets

IMPLANTABLE GLAUCOMA DRAINAGE DEVICE

PRIORITY CLAIM

The present application is a non-provisional patent application, claiming the benefit of priority of U.S. Provisional Application No. 61/133,699, filed on Jul. 1, 2008, entitled, "IMPLANTABLE GLAUCOMA DRAINAGE DEVICE PACKAGING."

FIELD OF INVENTION

The present invention relates to a glaucoma drainage device and, in particular, to a bio-compatible glaucoma drainage system packaged into a needle-implantable capillary tube.

BACKGROUND OF INVENTION

In the United States, it is estimated that 2.2 million people age 40 and older have glaucoma, with 120,000 suffering blindness [1] (see List of Cited References, below). Most glaucoma patients are associated with abnormally high intraocular pressure (IOP) due to the patient's inability to drain excessive aqueous humor from the anterior chamber of the eye through the trabecular meshwork. If not reduced with adequate treatment, the high IOP would continuously suppress and damage the optic nerve as the disease progresses, leading to loss of vision or even total blindness. Current clinical treatment involves medication typically in the form of eye drops with dosages depending on the severeness of the disease. However, this treatment is accompanied by certain concerns such as difficulty of continuous treatment, inefficient dosage style, and potential side effects or patient refractoriness to the drug composition. Glaucoma drainage devices (GDD) present a potentially desirable alternative to continuous treatment with eye drops. GDD's function by providing an artificial drainage path so as to reduce the IOP. GDD's usually comprise a plurality of valves to regulate IOP within a prescribed range. Different kinds of on-chip surface-micromachined parylene-based check valves have been investigated with the potential application of using them as IOP regulators. The aforementioned technology, however, does not exist as a stand-alone device which can be implanted in a patient's eye in a minimally-evasive manner.

Thus, a continuing need exists for an implantable glaucoma drainage device which can regulate intraocular pressure.

List of Cited References:

[1] Glaucoma Research Foundation, www.glaucoma.org

[2] P. J. Chen, D. C. Rodger, E. M. Meng, M. S. Humayun, and Y. C. Tai, "Surface Micromachined Parylene Dual Valves for On-Chip Unpowered Microflow Regulation," *J. Microelectromech. Syst.*, vol. 16, pp. 223-231, 2007.

[3] P. J. Chen, and Y. C. Tai, "Floating-Disk Parylene Micro Check Valve," *Proc. MEMS 2007 Conference*, Kobe, Japan, Jan. 21-55, 2007, pp. 453-456.

[4] P. J. Chen, D. C. Rodger, M. S. Humayun, Y. C. Tai, "Floating-Disk Parylene Microvalve for Self-Regulating Biomedical Flow Controls," *Proc. MEMS 2008 Conference*, Tucson, Ariz., USA, Jan. 13-17, 2008, pp. 575-578.

[5] P. J. Chen, D. C. Rodger, S. Saati, J. C. Altamirano, C. H. Lin, R. Agrawal, R. Varma, M. S. Humayun, and Y. C. Tai, "Implementation of microfabricated sutureless flexible parylene tissue anchors on minimally invasive biomedical implants," *Proc. MicroTAS 2007 Conference*, Paris, France, Oct. 7-11, 2007, pp. 518-520.

SUMMARY OF INVENTION

In one aspect, present invention relates to a glaucoma drainage device and, in particular, to a bio-compatible glaucoma drainage system packaged into a needle-implantable capillary tube. The device comprises a microflow control system, a protective hollow carrier tube for housing the microflow control system, and one or more anchoring arms for retaining the device in a desired position within a patient's eye. The microflow control system comprises one or more pressure-sensitive valves. Each valve has a pressure threshold at which it changes from a first configuration to a second configuration, where one of the two configurations is an opened configuration and the other is a closed configuration. When in the open configuration fluid is allowed to pass through the valve, and when in the closed configuration fluid is not allowed to pass through the valve. The device further comprises a protective hollow carrier tube having two opened ends though which fluid can pass, where the microflow control system is attached with and fitted inside the protective carrier tube. One or more anchoring arms is attached with an exterior of the protective carrier tube, the anchoring arms configured to retain the device in a desired position within a patient's eye. Thus, changes in intraocular pressure beyond a prescribed pressure threshold will cause the one or more valves of the device to change configurations, thereby allowing or disallowing fluid drain from the patient's eye.

In another aspect, the microflow control system comprises two valves connected with a coupling tube, where one valve is an opened normally-closed valve having a prescribed lower-limit threshold pressure and the other valve is a closed normally-opened valve having a prescribed upper-limit threshold pressure.

In yet another aspect, at least one of the ends of the protective hollow carrier tube is slanted to facilitate insertion into a patient's tissue.

In a further aspect, the present invention comprises a method for fabricating anchoring arms for a drainage device. First, photoresist is deposited onto a thermal oxide silicon substrate. Next, one or more notches is patterned into the photoresist. The pattern of notches is transferred onto the thermal oxide layer by an etching process. Then, semi-circular trenches are etched into the silicon wafer through the notches in the oxide layer. The oxide layer is then removed. A bio-compatible material is deposited across the substrate and semi-circular trenches as a structure layer. The structure layer is coated with an aluminum layer. Then, the structure layer is laminated with a dry film photoresist. Next, the dry film photoresist is patterned, leaving photoresist over the semi-circular trenches. Exposed portions of aluminum are etched off with aluminum etchant. Exposed portions of the structure layer are also etched to form separate structure layer regions. Any remaining aluminum is removed with aluminum etchant, and the separate structure layer regions are released as anchoring arms.

As can be appreciated by one skilled in the art, the present invention also comprises an anchoring arm for a drainage device formed by the above method.

In yet another aspect, the present invention comprises a method for testing a drainage device for relieving intraocular pressure, the device having a microflow control system, a protective hollow carrier tube, and one or more anchoring arms. The testing method comprises folding the one or more anchoring arms and inserting the drainage device at least partially into a testing tube. Then, the drainage device is sealed within the testing tube using photoresist or other sealant. The testing tube is connected to a fluid source controlled by a pressure regulator and monitored by a pressure gauge and flow meter. A testing fluid is run at various pressures through the testing tube and into the drainage device, whereby the drainage device can is tested for proper functioning at desired pressures.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a glaucoma drainage device and, in particular, to a bio-compatible glaucoma drainage system packaged into a needle-implantable capillary tube. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a glossary of terms used in the description and claims is provided. Next, a description of various principal aspects of the present invention is provided. Subsequently, an introduction provides the reader with a general understanding of the present invention. Finally, details of the present invention are provided to give an understanding of the specific aspects.

Figure 1:
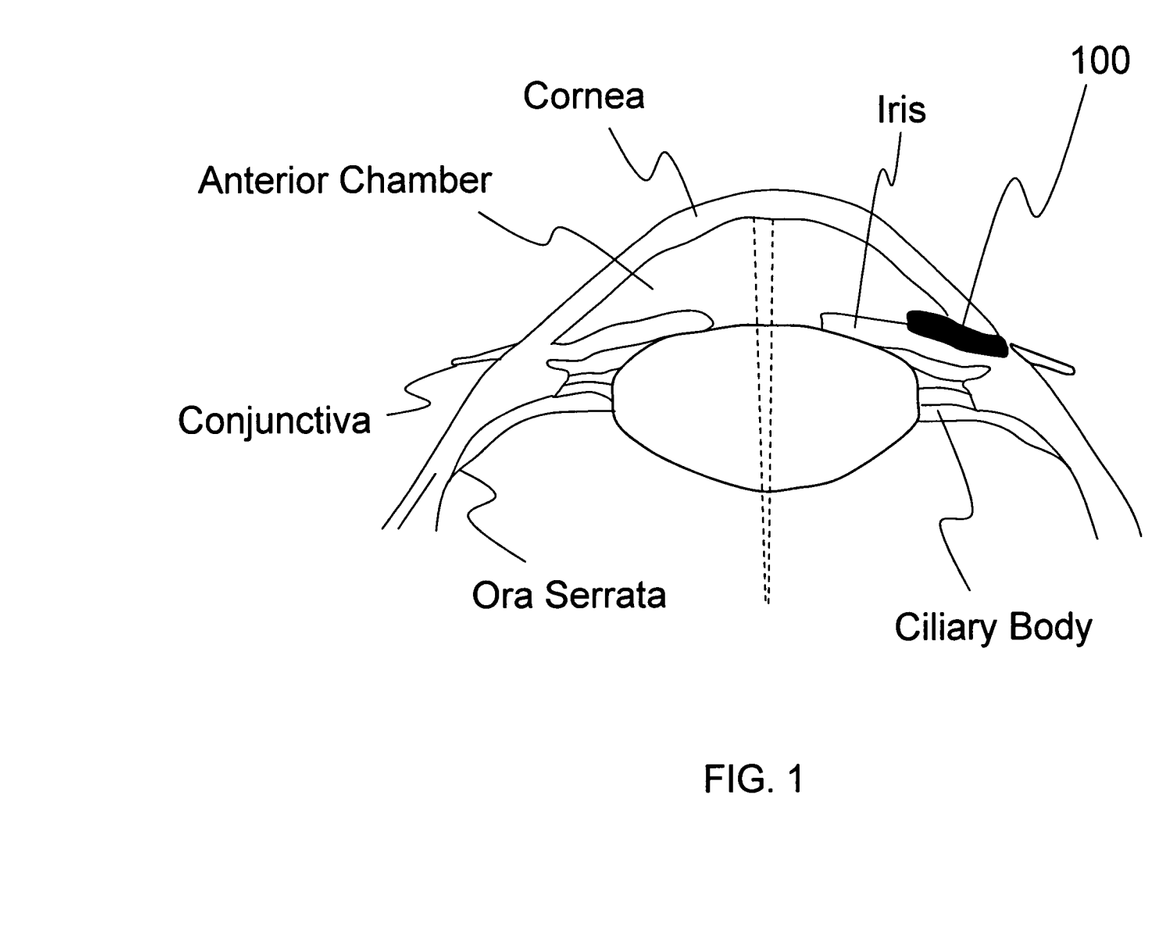
FIG. 1 is an illustration showing a glaucoma drainage device (GDD) in accordance with the present invention as implanted in a patient's eye.

(1) Glossary of Acronyms
BHF—Buffered Hydrofluoric Acid
DRIE—Deep Reactive Ion Etching
FET—Frozen Embryo Transfer
GDD—Glaucoma Drainage Device
HNA—Hydrofluoric, Nitric, and Acetic Acid
IOP—Intraocular Pressure (2) Description The present invention relates to a glaucoma drainage device and, in particular, to a bio-compatible glaucoma drainage device (GDD) system packaged into a needle-implantable capillary tube. The GDD system comprises a microflow control system for controlling intraocular pressure, a protective capillary carrier tube housing the microflow control system, and anchoring arms holding the implanted device in place. The overall GDD size can be in a needle-implantable form factor for minimally invasive implantation. The GDD may be implanted via subconjunctival needle implantation to mimic the normal aqueous humor drainage pathway. FIG. 1 shows a cross section diagram of a human eye with a GDD device 100 implanted subconjunctivally.

The microflow control system component of the present invention can contain either a single or dual micro check valves to regulate the aqueous humor without any external power consumption. The microflow control system provides band-pass like flow regulation behavior and further controls the intraocular pressure (IOP) drainage profile. The device is capable of regulating the intraocular pressure to be below approximately 20 mmHG without causing hypotony (i.e., IOP<5 mmHG). It is further desirable to have the valve closed if high IOP (e.g., IOP>50 mmHG) happens due to normal external interferences like eye rubbing or bumping. Therefore, it is desirable to have valves with function comprising an opened normally-closed (NC) valve above approximately 20 mmHG and a closed normally-open (NO) valve above approximately 50 mmHG in order to realize the appropriate pressure-bandpass flow regulation. It should be noted that the orientation of the valves is independent and can be changed depending on the target flow pattern. Also, the number of valves in the microflow control system can be changed and allocated depending on the valve function design and surgery needs.

Figure 2:
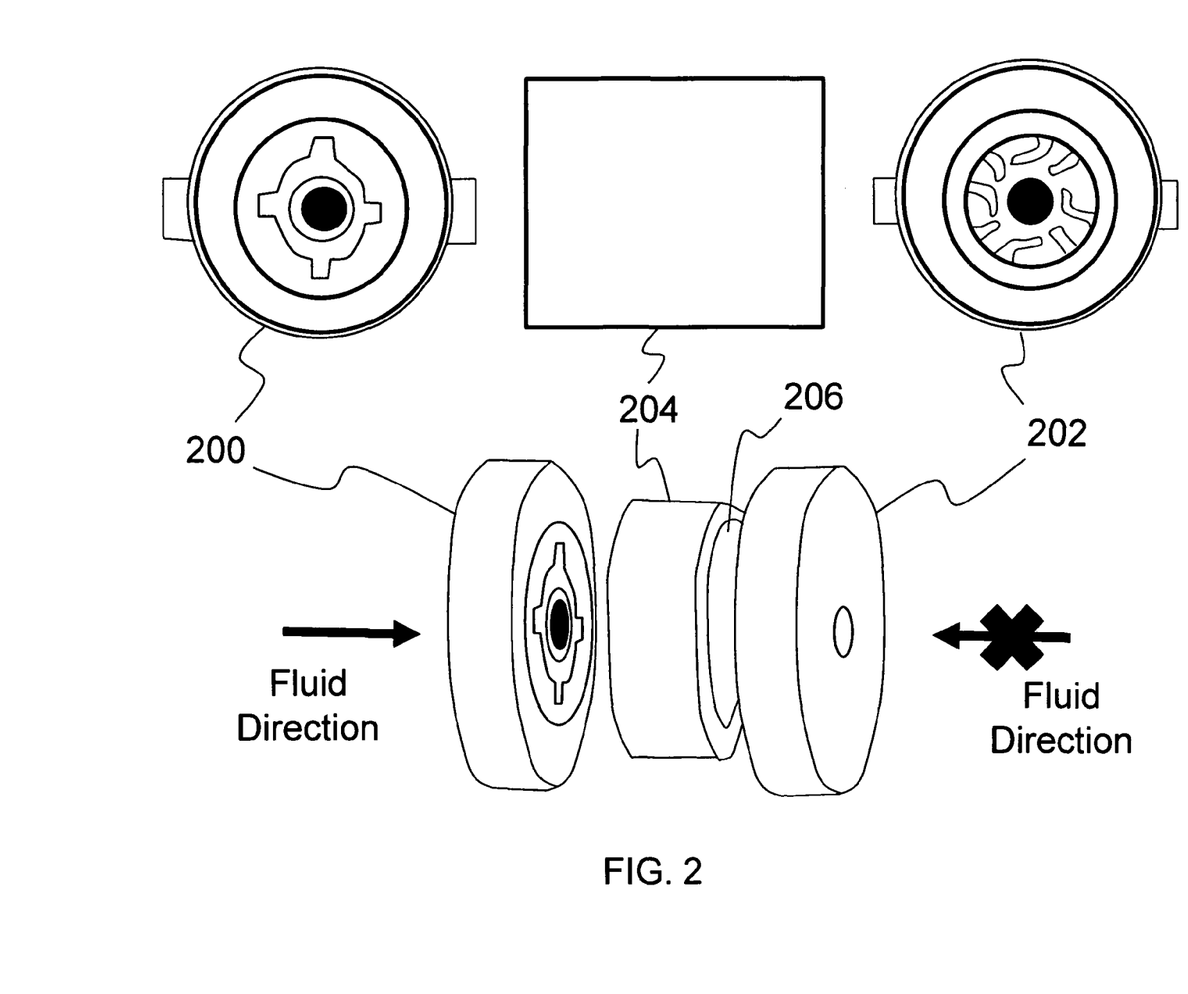
FIG. 2 is a set of illustrations showing the components of a microflow control system for use with the present invention.

FIG. 2 shows a schematic for the microflow control system comprising a NC-valve 200 for controlling the low-pressure-off response, a NO-valve 202 for controlling the high-pressure-open response, and a capillary tube serving as a coupling tube 204. The valves 200 and 202 are attached with the ends of the coupling tube 204 by a method such as but not limited to gluing. For ease of assembly, the valves 200 and 202 can be encircled by grooves formed by a method such as but not limited to deep reactive ion etching (DRIE). It is desirable for the valves to have a smaller planar size than an inner diameter 206 of the coupling tube so that the valve surface would not be contaminated during packaging and also to make it easier to load the microflow control system into the appropriate capillary tube carrier.

Figure 3:
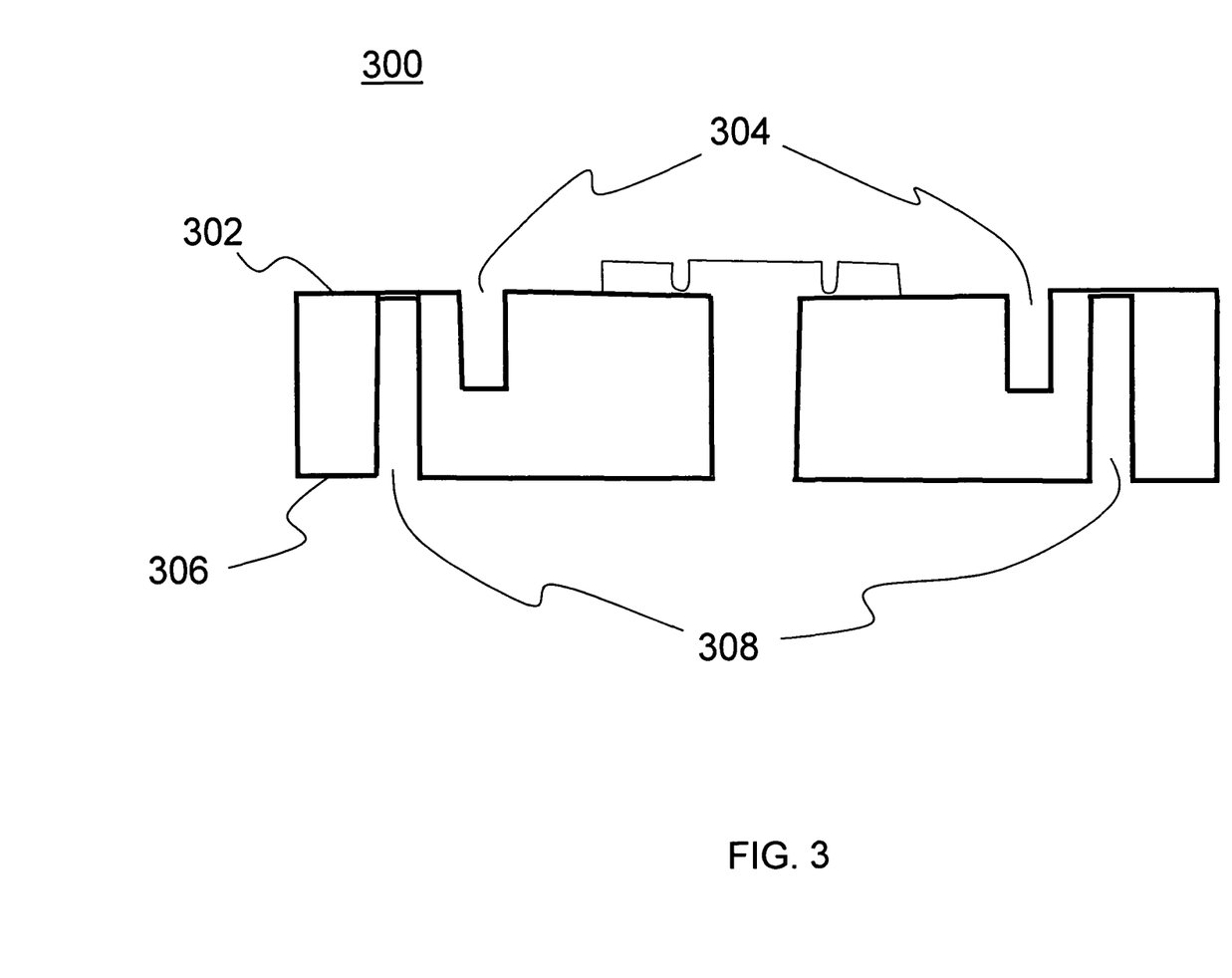
FIG. 3 is an illustration showing a diametrical cross section of a valve for use with the present invention.

FIG. 3 is an illustration showing a circumferential cross section of a valve 300 for use with the present invention. On a front side 302 of the valve wafer there is a circular coupling tube alignment groove 304 for fitting the valve with the coupling tube. On a back side 306 of the valve wafer is a circular valve releasing trench 308 to be introduced into a protecting hollow tube carrier during packaging of the device.

Figure 4:
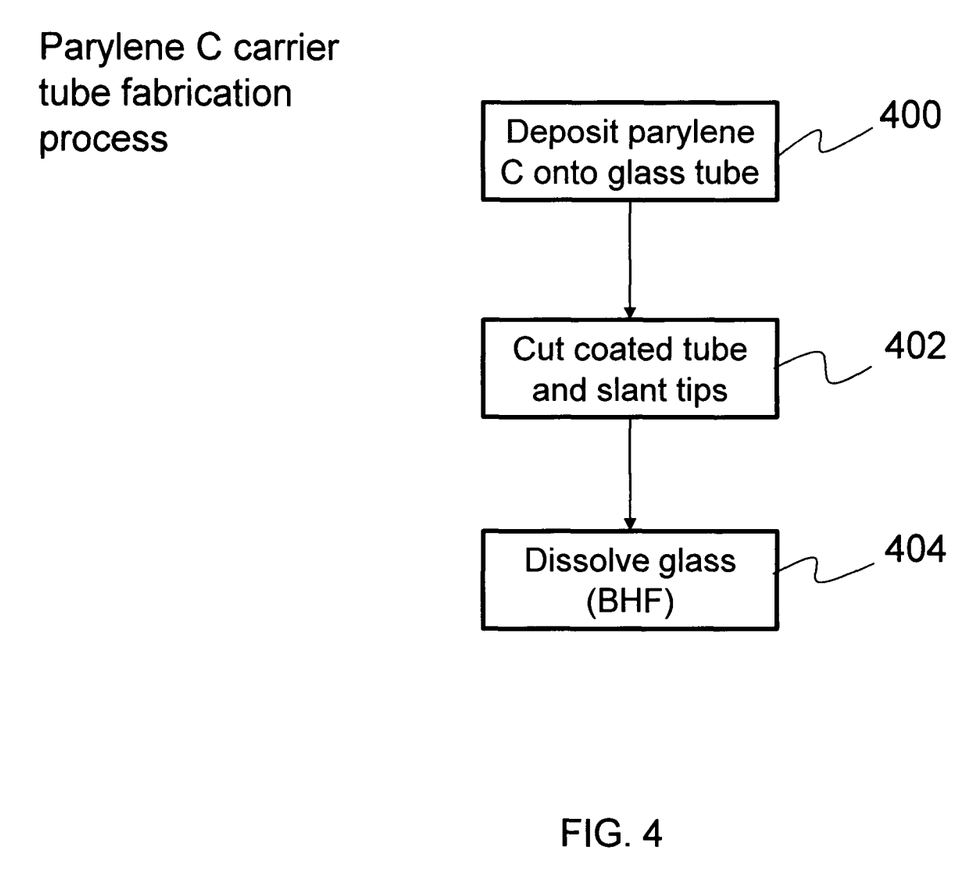
FIG. 4 is a flow diagram showing a parylene carrier tube fabrication process according to the present invention.

A protective capillary carrier tube can accommodate the microflow control system as described above, and can fit into a 19-gauge or smaller needle to facilitate hypodermic implantation. One or both tips of the protecting tube can be slanted for convenient device implantation at the subconjunctiva site. The length of the protecting tube can be trimmed to a desired length depending on the size of the individual eye. In a desired embodiment material of the protective carrier tube is glass coated with parylene C or pure parylene C for biocompatible needs, although other implantable-grade bio-compatible materials may be used. A fabrication method for a pure parylene type carrier tube is described below and represented by a flow chart in FIG. 4. First, a parylene C layer is deposited 400 onto the surface of a glass tube, such as a 40 μm glass tube. Next, the tube is cut 402 into proper length and slanted at the tip. Finally the glass is dissolved 404 by soaking in buffered hydrofluoric acid (BHF), leaving a pure parylene C carrier tube.

Figure 5A:
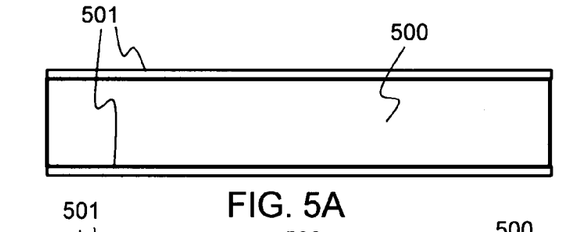
FIG. 5A is an illustration showing a lateral cross-section of an intermediate product in the fabrication of anchoring arms according to the present invention, where a silicon wafer is coated with an oxide layer.
Figures 5B, 5C:
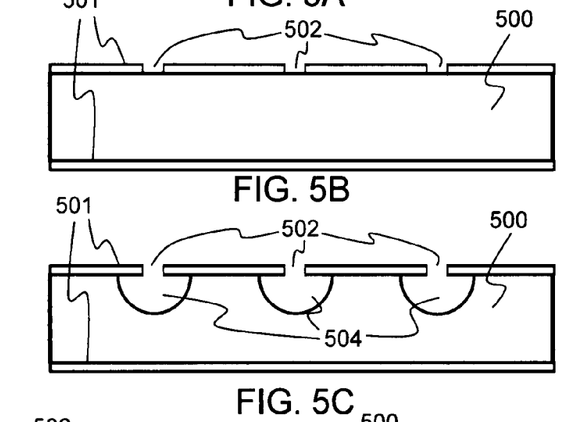
FIG. 5B is an illustration showing a lateral cross-section of an intermediate product in the fabrication of anchoring arms according to the present invention, where notches have been etched into the oxide layer.
FIG. 5C is an illustration showing a lateral cross-section of an intermediate product in the fabrication of anchoring arms according to the present invention, where trenches have been etched into a silicon substrate wafer with xenon difluoride.
Figure 5D:
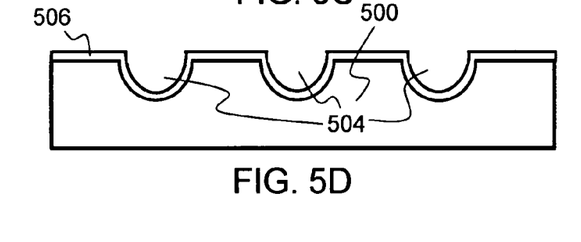
FIG. 5D is an illustration showing a lateral cross-section of an intermediate product in the fabrication of anchoring arms according to the present invention, where a parylene C layer has been deposited over the etched trenches in the substrate wafer.
Figure 5E:
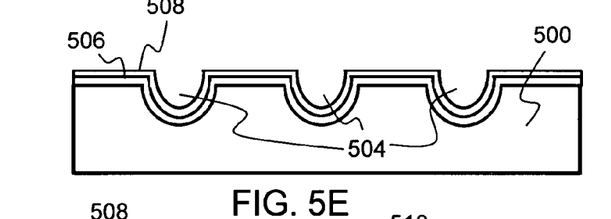
FIG. 5E is an illustration showing a lateral cross-section of an intermediate product in the fabrication of anchoring arms according to the present invention, where an aluminum layer is deposited over the parylene layer.
Figure 5F:
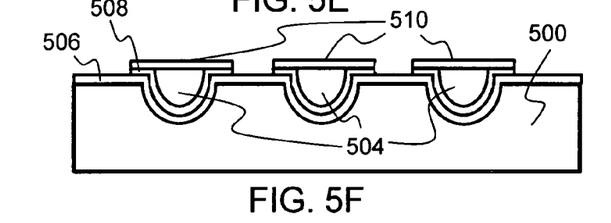
FIG. 5F is an illustration showing a lateral cross-section of an intermediate product in the fabrication of anchoring arms according to the present invention, where a second photoresist mask is deposited over the aluminum layer.
Figure 5G:
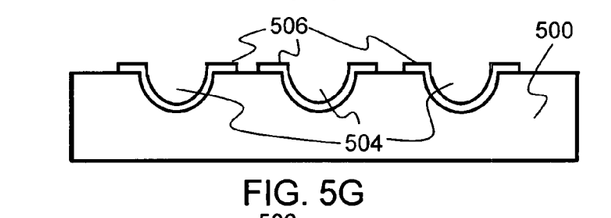
FIG. 5G is an illustration showing a lateral cross-section of an intermediate product in the fabrication of anchoring arms according to the present invention, where excess parylene and the aluminum layers have been removed, leaving separate parylene layers on the substrate wafer.
Figure 5H:
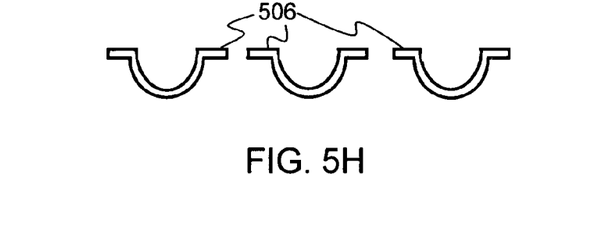
FIG. 5H is an illustration a lateral cross-section of three fabricated anchoring arms according to the present invention.

The GDD device of the present invention further comprises anchoring arms integrated at strategic positions to confine the GDD to a desired position where the arm tips are placed on both sides of the eye wall, preventing the GDD from migrating after implantation. The geometrical shape and length of the anchoring arms can be specifically tailored depending on the surgical needs. In a desired embodiment, the anchoring arms are made of parylene C, which makes them flexible and allows them to be folded into the needle hole for implantation and then unfold after implantation. In this manner, the GDD device is anchored at the implantation site. A fabrication method for the anchoring arms is described below and shown pictorially in FIGS. 5A-5H. It should be noted that the specific fabrication acts described below describe a preferred embodiment and are not to be construed as a limiting. In particular, materials, dimensions, and shapes described below should be construed as non-limiting examples of a preferred embodiment of the method. The fabrication method begins with a silicon wafer 500 having an approximately 1 μm thermal oxide layer 501, as shown in FIG. 5A. A photoresist layer is then deposited onto the thermal oxide layer 501 by spin coating or other known technique. The photoresist is patterned by photolithography, and transferred on the front side by BHF etching, leaving notches in the thermal oxide layer 501 of the silicon wafer as shown in FIG. 5B. In FIG. 5C, the notches 502 in the oxide layer are etched by xenon difluoride, forming trenches 504 beneath the oxide layer. The oxide layer is then removed by BHF etching and an approximately 25 μm parylene coat 506 is applied to the wafer 500 as shown in FIG. 5D. Then, in FIG. 5E parylene layer 506 is then coated with Aluminum 508 by thermal evaporation to a thickness of approximately 3 μm. Next, as shown in FIG. 5F, the dry film is laminated with a second photoresist, patterned by photolithography and etched by aluminum etchant, leaving a protecting photoresist mask 510 over the now parylene-coated trenches 504. In FIG. 5G, the excess parylene is removed by oxygen plasma etching and the aluminum is removed by aluminum etchant, leaving only separated parylene layers 506 coating the trenches 504. These parylene layers 506 are the anchoring arms in the GDD device. Finally, the parylene layers 506 can be released as fabricated anchoring arms by HNA (hydrofluoric, nitric, and acetic acid).

Figure 6A:
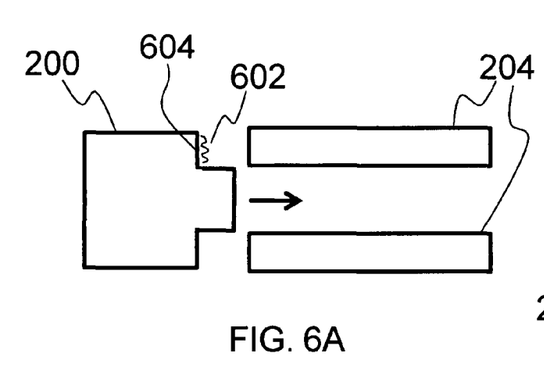
FIG. 6A is an illustration showing a mechanism for affixing a first pressure valve with a coupling tube.
Figure 6B:
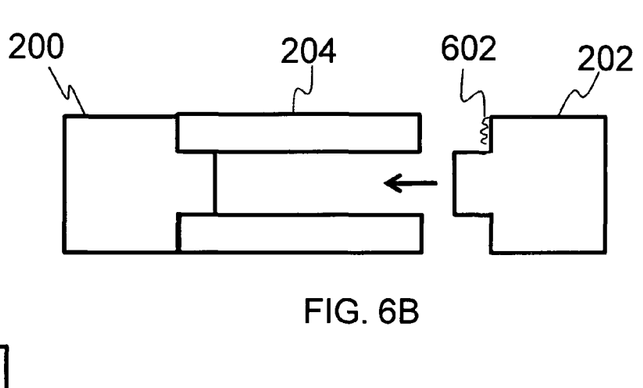
FIG. 6B is an illustration showing a mechanism for affixing a second pressure valve with a coupling tube.
Figure 6C:
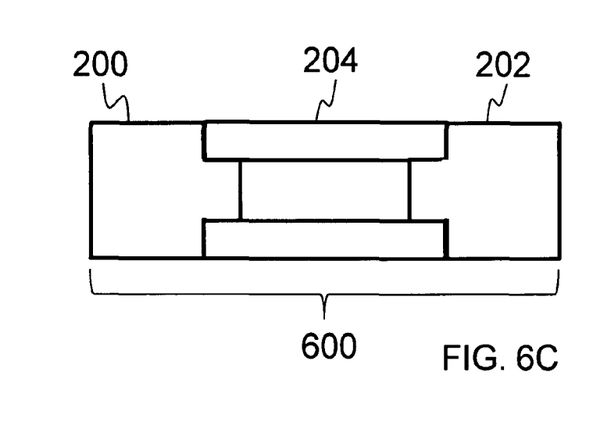
FIG. 6C is an illustration showing a formed microflow control system according to the present invention.

The microfabricated valves are packaged into a capillary coupling tube to fulfill the microflow control system. FIG. 6A is a cross sectional illustration showing the assembly procedure for affixing a check valve 200 to a coupling tube 204 with an epoxy 602 or other bio-compatible adhesive. It should be noted that other affixing methods besides gluing with epoxy are possible, including but not limited to temperature-assisted bonding, laser-assisted bonding, plasma or reactive ion assisted bonding, etc. The epoxy 602 is applied to an outer perimeter 604 of the check valve 200, and then the valve is placed in contact with the coupling tube 204. A second valve can be affixed to the coupling tube as shown in FIG. 6B. The second valve 202 is affixed to the coupling tube 204 with epoxy 604 in the same manner as the first valve 200. A cross section of a complete microflow control system 600 is shown in FIG. 6C.

Figure 7A:
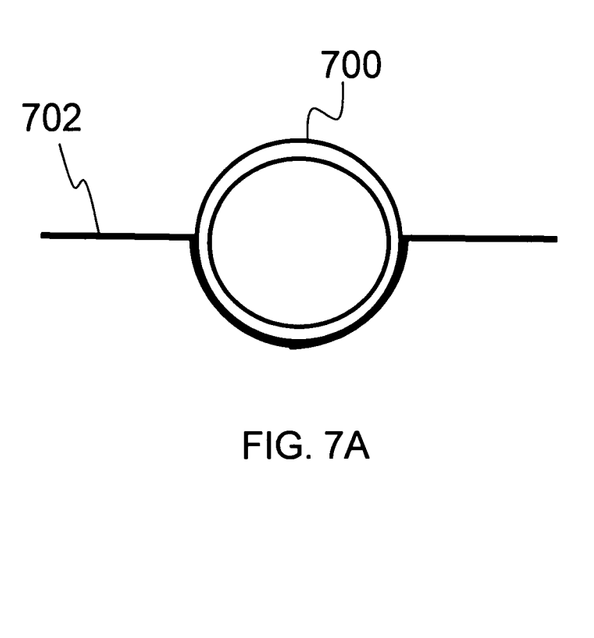
FIG. 7A is an illustration showing a cross-section of a protective carrier tube attached with an anchoring arm according to the present invention.
Figure 7B:
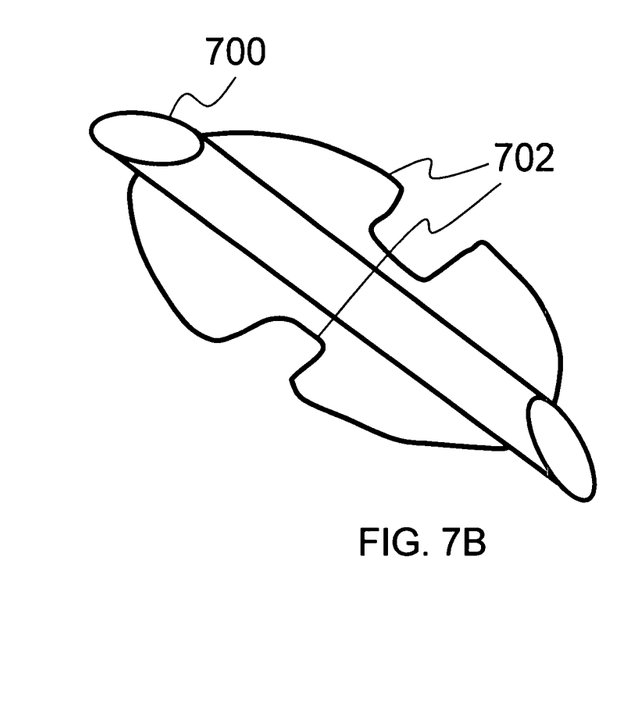
FIG. 7B is an illustration showing a perspective view of a protective carrier tube attached with an anchoring arm according to the present invention.

The protective carrier tube which will eventually house the microflow control system must be assembled with the anchoring arms. The carrier tube can be affixed to the anchoring arms methods including but not limited to gluing with epoxy. The entire apparatus can then be coated with 1 μm of epoxy. FIG. 7A illustrates a cross sectional view of the protective carrier tube 700 attached with the anchoring arms 702. FIG. 7B is an isometric view of the protective carrier tube 700 attached with the anchoring arms 702.

Figure 8A:
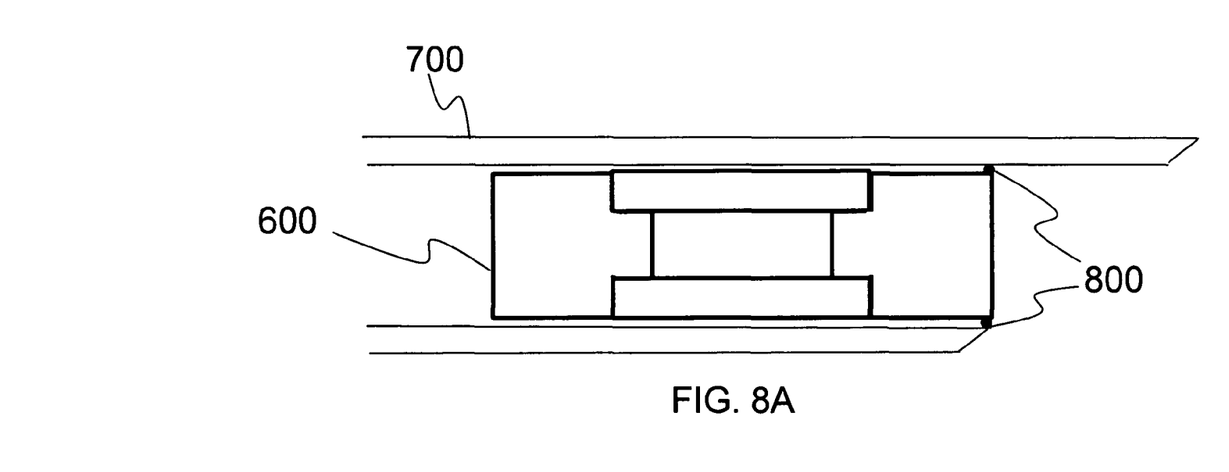
FIG. 8A is an illustration showing a cross-section of a microflow control system housed within a protective carrier tube.
Figure 8B:
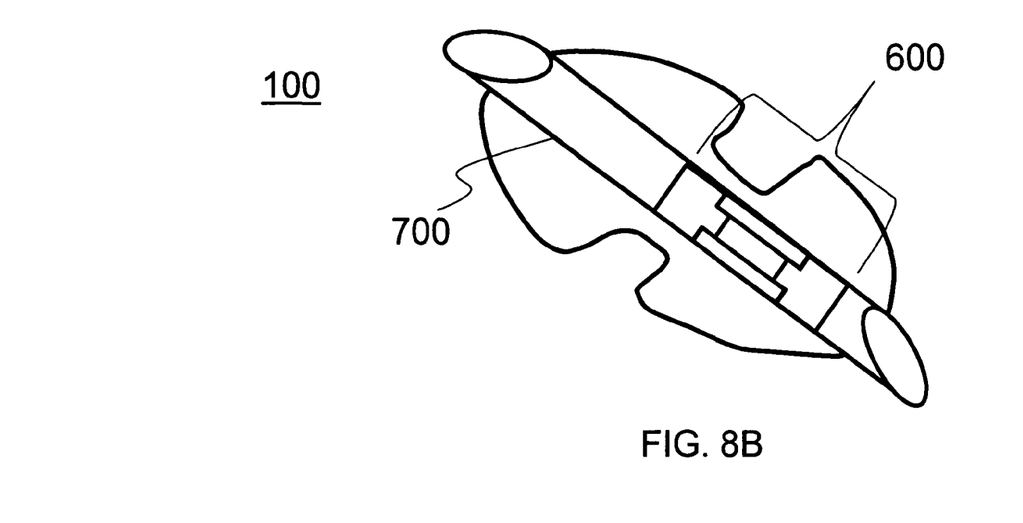
FIG. 8B is an illustration of a fully-formed GDD system according to the present invention.

The microflow control system is incorporated with the device by sealing it with epoxy into the protective hollow tube carrier. FIG. 8A illustrates a lateral cross section view of the microflow control system 600 fitted into the protective carrier tube 700 and affixed with epoxy 800. It should be noted that other affixing methods besides gluing with epoxy are possible, including but not limited to temperature-assisted bonding, laser-assisted bonding, plasma or reactive ion assisted bonding, etc. FIG. 8B illustrates a perspective view of the completed GDD device 100 with the protective carrier tube 700 shown as transparent to view the microflow control system 600 housed inside.

Figure 9:
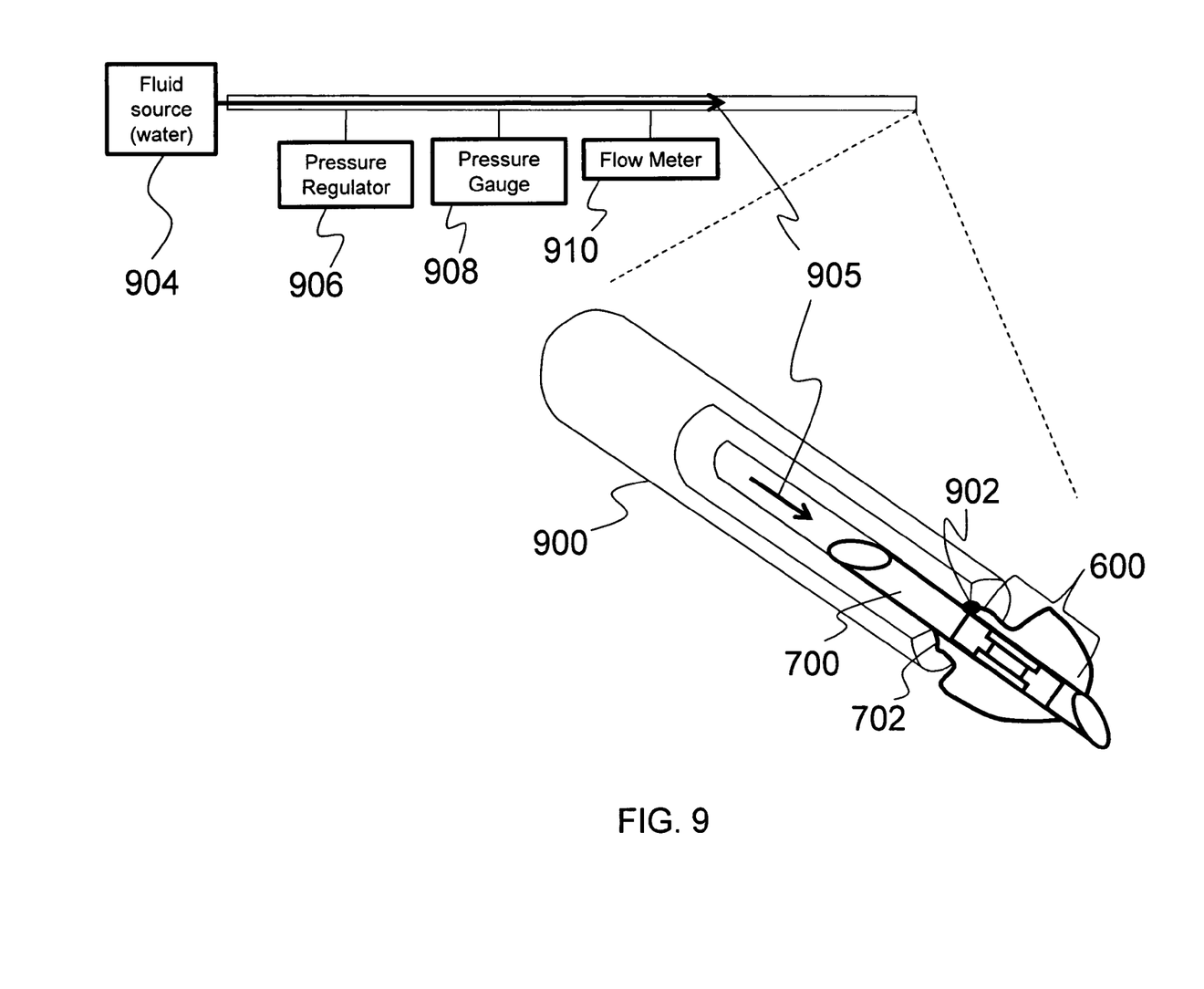
FIG. 9 is an illustration showing a system for testing a GDD system in accordance with the present invention.

To test the function of the GDD, the anchoring arms 702 are folded and then the completed system is inserted into another larger tube such as, but not limited to, a frozen embryo transfer (FET) tube 900, and sealed by photoresist 902, as shown in FIG. 9. Note, the FET tube 900 is shown as partially cut-away for ease of viewing. The sealing photoresist 902 can be either developed or undeveloped depending on whether it is going to be stripped with the photoresist within the microflow control system 600 simultaneously. The photoresist can be stripped by acetone, isopropyl alcohol and de-ionized water to release the overall GDD system 100 for later surgery implantation. To test the GDD device 100, a fluid source 904 feeds a fluid 905 such as water into the FET tube 900, which is stoppered by the GDD 100. A pressure regulator 906 regulates the source flow. The pressure and flow in the tube can be measured using a pressure gauge 908 and flow meter 910.

What is claimed is:

1. A device for relieving intraocular pressure, comprising:
    a microflow control system comprising at least one pressure-sensitive valve, where the at least one pressure-sensitive valve has a pressure threshold at which it changes from a first configuration to a second configuration, where one of the two configurations is an opened configuration and the other is a closed configuration, such that when in the open configuration fluid is allowed to pass through the at least one pressure-sensitive valve, and when in the closed configuration fluid is prevented from passing through the at least one pressure-sensitive valve;
    a protective hollow carrier tube having two opened ends though which fluid can pass, where the microflow control system is attached with and fitted inside the protective carrier tube; and
    a pair of foldable anchoring arms having rounded edges and opposingly attached with an exterior of the protective carrier tube, wherein each folding anchoring arm of the pair of foldable anchoring arms comprises as set of rounded arm tips to retain the device in as desired position within a patient's eye, such that a set of rounded arm tips is placed on each side of an eye wall of the patient;
    wherein the device is configured such that changes in intraocular pressure beyond a prescribed pressure threshold will cause the at least one pressure-sensitive valve of the device to change configurations, thereby allowing or disallowing fluid drain from the patient's eye.

2. The device of Claim 1, wherein the microflow control system comprises two valves connected with a coupling tube, where one valve is an opened normally-closed valve having a prescribed lower-limit threshold pressure and the other valve is a closed normally-opened valve having a prescribed upper-limit threshold pressure.

3. The device of claim 2, wherein at least one of the ends of the protective hollow carrier tube is slanted to facilitate insertion into a patient's tissue.

4. The device of Claim 1, wherein at least one of the ends of the protective hollow carrier tube is slanted to facilitate insertion into a patient's tissue.

\* \* \* \* \*